United States Patent
Yim et al.

(10) Patent No.: US 10,265,232 B2
(45) Date of Patent: Apr. 23, 2019

(54) PREFABRICATED MODULAR RADIATION THERAPY VAULT DESIGN

(71) Applicant: Varian Medical Systems Trading (Beijing) Co., Ltd., Beijing (CN)

(72) Inventors: Chung Chee Yim, Hong Kong (CN); Wan Fang Li, Beijing (CN); Ying Sun Au, Hong Kong (CN); Raymond Pau, Hong Kong (CN); Qian Hua Xu, Guangzhou (CN); Takashi Niimi, Yokohama (JP)

(73) Assignee: Varian Medical Systems Trading (Beijing) Co., Ltd., Beijing (CN)

( * ) Notice: Subject to any disclaimer, the term of this patent is extended or adjusted under 35 U.S.C. 154(b) by 0 days.

(21) Appl. No.: 15/553,158

(22) PCT Filed: Mar. 17, 2016

(86) PCT No.: PCT/IB2016/000310
§ 371 (c)(1),
(2) Date: Aug. 23, 2017

(87) PCT Pub. No.: WO2016/147047
PCT Pub. Date: Sep. 22, 2016

(65) Prior Publication Data
US 2018/0110666 A1    Apr. 26, 2018

(30) Foreign Application Priority Data
Mar. 17, 2015  (CN) .......................... 2015 1 0116982

(51) Int. Cl.
*E04B 1/92*      (2006.01)
*A61G 10/00*     (2006.01)
(Continued)

(52) U.S. Cl.
CPC ........... *A61G 10/00* (2013.01); *A61N 5/1028* (2013.01); *E04B 1/34315* (2013.01); *E04B 1/92* (2013.01);
(Continued)

(58) Field of Classification Search
CPC ...... A61G 10/00; A61G 2210/50; E04B 1/92; E04B 2001/925; E04B 1/34315;
(Continued)

(56) References Cited

U.S. PATENT DOCUMENTS 3,696,805 A * 10/1972 Sweeten ................. E04B 1/346
                                                    600/301
4,723,383 A *  2/1988 Jenn ........................ E04B 7/107
                                                    52/309.4
(Continued)

FOREIGN PATENT DOCUMENTS

CN       1959858 A       5/2007
CN     101554853 A      10/2009
(Continued)

OTHER PUBLICATIONS

PCT, International Search Report and Written Opinion in International Application No. PCT/IB2016/000310, dated Jul. 26, 2016 (10 pages).

*Primary Examiner* — Babajide A Demuren (57) ABSTRACT

A radiotherapy center includes a treatment room and a radiation machine located in the treatment room. The treatment room is constructed with materials comprising a plurality of prefabricated, modular radiation shielding blocks. The radiotherapy center may further include a plurality of functional rooms adjacent to the treatment room. The plurality of functional rooms may be constructed from a plu-
(Continued)

rality of prefabricated modules. The plurality of functional rooms may be arranged in a quadrangle configuration, surrounding a central atrium.

25 Claims, 8 Drawing Sheets

(51) Int. Cl.
    *E04H 3/08*     (2006.01)
    *A61N 5/10*     (2006.01)
    *E04B 1/343*     (2006.01)
    *E04C 1/40*     (2006.01)

(52) U.S. Cl.
    CPC ............... *E04C 1/40* (2013.01); *E04H 3/08* (2013.01); *A61G 2210/50* (2013.01); *A61N 2005/1094* (2013.01); *E04B 2001/925* (2013.01)

(58) Field of Classification Search
    CPC .......... A61N 2005/1094; A61N 5/1028; E04C 1/40; E04H 3/08
    See application file for complete search history.

(56) References Cited

U.S. PATENT DOCUMENTS

| | | | | |
|---|---|---|---|---|
| 5,035,098 A * | 7/1991 | Newsom | ............... | E04C 1/40 |
| | | | | 52/421 |
| 5,695,443 A * | 12/1997 | Brent | ............... | G21F 1/02 |
| | | | | 405/129.55 |
| 6,973,758 B2 * | 12/2005 | Zeik | ............... | A61N 5/10 |
| | | | | 52/169.6 |
| 7,665,249 B2 * | 2/2010 | Zeik | ............... | A61N 5/10 |
| | | | | 52/79.1 |
| 7,728,315 B2 * | 6/2010 | Bichay | ............... | G21F 7/00 |
| | | | | 250/505.1 |
| 8,112,942 B2 * | 2/2012 | Bohm | ............... | E04H 3/08 |
| | | | | 52/220.1 |
| 8,695,299 B2 * | 4/2014 | Propst | ............... | B32B 5/18 |
| | | | | 52/309.11 |
| 9,027,297 B2 * | 5/2015 | Lefkus, III | ............... | A61N 5/10 |
| | | | | 52/234 |
| 9,171,649 B2 * | 10/2015 | Zeik | ............... | A61N 5/10 |
| 9,183,957 B2 * | 11/2015 | Farrell | ............... | G21F 1/04 |
| 9,308,141 B2 * | 4/2016 | Blackwell | ............... | A61G 3/001 |
| 9,575,148 B2 * | 2/2017 | Winter | ............... | G01R 33/3802 |
| 2002/0166293 A1 | 11/2002 | Zeik | | |
| 2004/0025448 A1 * | 2/2004 | Puusepp | ............... | G21F 3/00 |
| | | | | 52/64 |
| 2008/0203331 A1 * | 8/2008 | Murphy | ............... | A61N 5/10 |
| | | | | 250/517.1 |
| 2008/0276554 A1 | 11/2008 | Sheetz | | |
| 2013/0082196 A1 * | 4/2013 | Farrell | ............... | G21F 1/00 |
| | | | | 250/496.1 |
| 2013/0111825 A1 | 9/2013 | Lefkus, III | | |
| 2015/0240473 A1 * | 8/2015 | Lefkus, III | ............... | A61N 5/10 |
| | | | | 52/79.1 |
| 2015/0328432 A1 * | 11/2015 | Liu | ............... | A61G 10/00 |
| | | | | 600/27 |
| 2016/0038766 A1 * | 2/2016 | Zeik | ............... | A61N 5/10 |
| | | | | 600/1 |
| 2016/0130795 A1 * | 5/2016 | Downey | ............... | E04H 5/00 |
| | | | | 52/79.1 |
| 2018/0258659 A1 * | 9/2018 | LeBlanc | ............... | E04H 3/08 |

FOREIGN PATENT DOCUMENTS

| | | | | |
|---|---|---|---|---|
| JP | H02173600 A | 7/1990 | | |
| WO | WO-2011146573 A1 * | 11/2011 | ............... | G21F 1/00 |

* cited by examiner

PREFABRICATED MODULAR RADIATION THERAPY VAULT DESIGN

TECHNICAL FIELD

Embodiments of this disclosure relate generally to radiotherapy center design and construction. In particular, various embodiments of a prefabricated, modular radiotherapy center are described.

BACKGROUND

Radiation machines such as medical linear accelerators (LINACs) are useful in producing high energy radiation to treat patients with cancer. Depending on the type of cancer, position, size of the tumor and its surrounding critical organs, and the patient size, medical LINACs may operate at energies ranging from about 4 MV to about 20 MV for radiation therapy procedures. To protect staff and the general public, a radiation vault in which a LINAC is located must be carefully designed and constructed to adequately attenuate the radiation to an acceptable level outside the radiation vault.

Conventionally, the radiation vault is constructed on site with concrete using a pour-in-place method. The conventional method is time-consuming, typically taking more than 12-18 months on planning and construction. Further, instances such as inconsistence of density of the concrete mix, honey comb, cold joints, and poor workmanship may occur during conventional on-site construction and as such, the radiation vault constructed may not pass the initial safety test, resulting in beefing up of the structure and potential delay of treatment.

Accordingly, there is a general need for a method of constructing radiation vaults and associated facilities that allows significant reduction on time from planning and construction to treatment readiness, reduction of construction activities on site, and better quality assurance. There is a need for a method of constructing a radiotherapy center that can provide flexible design and scalability for future extension. There is a need for a method of constructing a radiotherapy center in areas or countries where skilled construction workforce and resources are scarce and/or construction licenses are restricted.

SUMMARY

Certain embodiments of a radiotherapy center, radiation vault, prefabricated shielding block, and method of constructing a radiotherapy center are set forth below. It should be understood that these embodiments are presented merely to provide the reader with a brief summary of certain forms the invention might take and that these embodiments are not intended to limit the scope of the invention. Indeed, the invention may encompass a variety of embodiments or aspects that may not be set forth below.

In one aspect, a radiotherapy center includes a treatment room and a radiation machine located in the treatment room. The treatment room is constructed with materials comprising a plurality of prefabricated, modular radiation shielding blocks. In some embodiments, the radiotherapy center further includes a plurality of functional rooms adjacent to the treatment room. The plurality of functional rooms may be constructed from a plurality of prefabricated modules. The plurality of functional rooms may be arranged in a quadrangle configuration, surrounding a central atrium.

In some embodiments, the plurality of functional rooms may be arranged such to provide a patient flow and a clinician flow that is separated from the patient flow. One or more corridors may be provided between the plurality of functional rooms and the central atrium. The one or more corridors may include a glass structure on a side adjacent to the central atrium to allow natural light to transmit into the one or more corridors, and/or one or more doors to allow access to the central atrium.

In another aspect, a building structure includes a room to be occupied by a radiation machine and a subject to be treated by the radiation machine, and a plurality of prefabricated, modular radiation shielding blocks enclosing the room. The plurality of prefabricated, modular radiation shielding blocks may be configured to adequately attenuate radiation generated by the radiation machine. The prefabricated, modular radiation shielding blocks are stackable and may be joined together in such a way that there is no direct straight line of passage through the joins. The prefabricated, modular radiation shielding blocks and modules may be sized in certain units and assembled to form the entire envelope of the room. The prefabricated, modular radiation shielding blocks may be made of a material comprising cement and high density quartz.

In a further aspect, a radiation shielding module is provided. The radiation shielding module is prefabricated by stacking a plurality of radiation shielding blocks and transportable to a site for constructing a treatment room for radiotherapy. The radiation shielding module is configured to adequately attenuate radiation generated by a radiation machine to be occupied in the treatment room. The radiation shielding modules may be made of a material comprising cement and high density quartz.

In a further aspect, a method of constructing a radiotherapy center is provided. In the method, a plurality of prefabricated, modular radiation shielding blocks are provided to a site selected for the radiotherapy center. A treatment room is constructed using at least some of the plurality of prefabricated, modular radiation shielding blocks. A radiation machine is provided in the treatment room. The plurality of prefabricated, modular radiation shielding blocks may be fabricated in a factory and transported to the site using e.g. a 20-foot container or a 40-foot container. In some embodiments, the method further includes providing a plurality of prefabricated modules to the site, and constructing a plurality of functional rooms adjacent to the treatment room using at least some of the plurality of prefabricated modules. The plurality of prefabricated modules may be fabricated in a factory and transported to the site using e.g. a 20-foot container or a 40-foot container.

Other aspect or embodiments are further described herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Various embodiments of methods for designing and constructing a radiotherapy center are described. It is to be understood that the disclosure is not limited to the particular embodiments described as such may, of course, vary. An aspect described in conjunction with a particular embodiment is not necessarily limited to that embodiment and can be practiced in any other embodiments. For instance, various embodiments are presented with a medical linear accelerator configured to generate high energy electrons and/or x-rays. It will be appreciated that the disclosed methods can be implemented with other types of radiation machines and systems producing other types of radiation such as gamma rays, protons, and other heavy ions or particles etc.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. In the following description, well known components or steps may not be described in detail in order to avoid unnecessarily obscuring the embodiments of the disclosure.

As used herein, the phrase "radiation vault," "banker," or "treatment room" refers to a room in which a radiotherapy machine is located for carrying out irradiation on a subject such as a patient in the room.

As used herein, the phrase "functional room" refers to a room in a radiotherapy center that can be used to provide one or more functions of treatment planning, treatment control, conferencing, resting, waiting, changing, cleaning, staff storing or the like. By way of example, a functional room may include, and is not limited to, an office, a nurse station, a treatment planning room, a treatment control room, a reception station, a waiting room, a changing room, an exam room, a restroom, a storage room, a cleaning room, etc.

As used herein, the term "modular" refers to an embodiment that a radiation shielding block of the disclosure is prefabricated in a factory and transportable to a site for assembling with other prefabricated radiation shielding blocks in constructing a treatment room.

As used herein, the phrase "transportable" refers to an embodiment that the prefabricated, modular radiation shielding blocks or functional modules of the disclosure can be transported by air, sea, or land to a site for radiotherapy center construction.

As used herein, the phrase "adequately attenuate radiation" refers to an embodiment that the treatment room constructed with the prefabricated modular radiation shielding blocks of the disclosure ensures that the radiation dose levels to the public and occupational personnel outside the treatment room are maintained below the limits as regulated by a state government or as recommended by a national or international organization. For example, in the United States, the radiation dose limits for the public and occupational personnel are regulated pursuant to 10 C.F.R. § 20. The radiation dose limits may be expressed as a weekly or yearly value. For example, the radiation dose limits can be below 0.02 mGy per week for uncontrolled areas or 0.1 mGy per week for controlled areas. A controlled area refers to a limited-access area in which the occupational exposure of personnel to radiation is under the supervision of an individual in charge of radiation protection. The access, occupancy, and working conditions are controlled for radiation protection purposes. An uncontrolled area refers to any space not meeting the definition of controlled area. The modular radiation shielding blocks of this disclosure can be engineered, constructed, or configured, e.g. through a combination of the materials used and the thickness of the shielding blocks, and based on the energy specification of the radiation machine located in the treatment room, the workload, the use factor, occupancy factor, etc., such that the treatment room constructed by the modular radiation shielding blocks can adequately attenuate radiation to maintain the radiation dose levels outside the treatment room below the limits required by the government or organization.

In general, this disclosure describes a design and construction of a radiotherapy center that can provide a solution for fast delivery of radiotherapy treatment. The radiotherapy center includes a radiation banker and various clinical functional modules which can be pre-engineered and prefabricated in a factory. The design allows significant reduction on time from planning and construction to treatment readiness. According to this disclosure, it takes only about two to three months and in some cases only about four weeks, depending on the scale of the project, to build a radiotherapy center for treatment readiness, including production of the prefabricated, modular radiation shielding blocks and prefabricated functional modules and site assembly. This is compared to conventional construction method which usually takes more than 12-18 months on planning and construction. Further, the disclosed method significantly reduces construction activities on site.

Many of the elements for the radiation bunker can be built in a controlled factory environment. As such, coordination of design, planning, site construction activities, and quality issues can be significantly minimized. Suitable software for shielding calculation and proven shielding materials and methodology can be used in engineering the shielding blocks in the factory according to the machine energy specification, the workload, the use factor, occupancy factor, etc. With the proper design, supervision and installation, the shielding performance of the radiation bunker can be guaranteed.

The ancillary facilities or rooms can be designed in modules and prefabricated in a factory. The prefabricated, functional modules can be configured to provide flexibility in design and are capable for future extension. The overall layout can be designed such that the patient's flow and clinician's work flow can be separated to avoid crowd and increase efficiency.

The prefabricated design is cost effective, quality controlled under factory environment and repeatable. The design allows for the flexibility for the customer to choose the combination as a standalone radiotherapy center or alternatively as an extension from an existing hospital. The design provides a solution for remote areas where there are transportation limitation and scarcity of skilled construction workforce and resources, and for countries where there are construction license restrictions.

Exemplary embodiments of methods for designing and constructing a radiotherapy center will now be described with reference to the figures. It should be noted that some figures are not necessarily drawn to scale. The figures are only intended to facilitate the description of specific embodiments, and are not intended as an exhaustive description or as a limitation on the scope of the disclosure.

Figure 1:
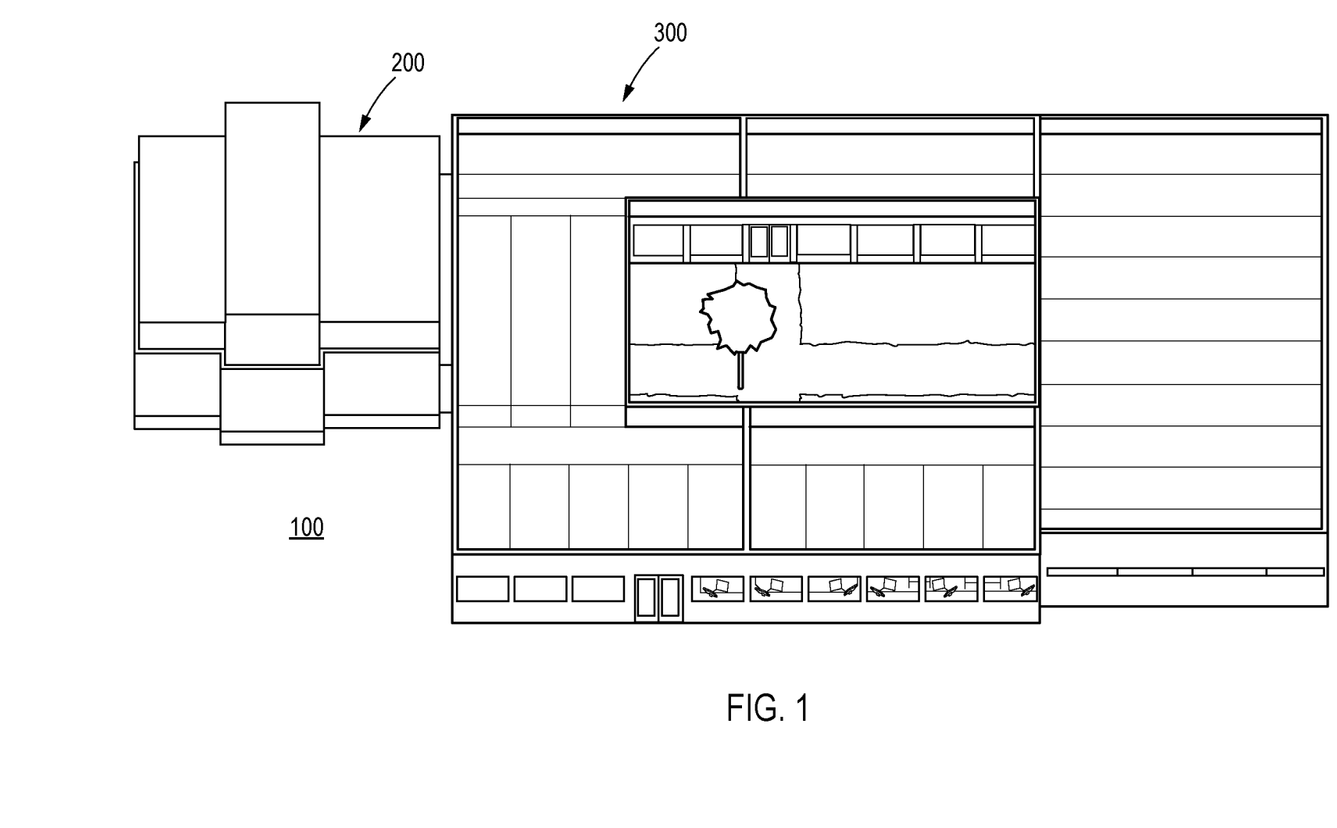
FIG. 1 is a perspective view of a radiotherapy center according to some embodiments of the disclosure.
Figure 2:
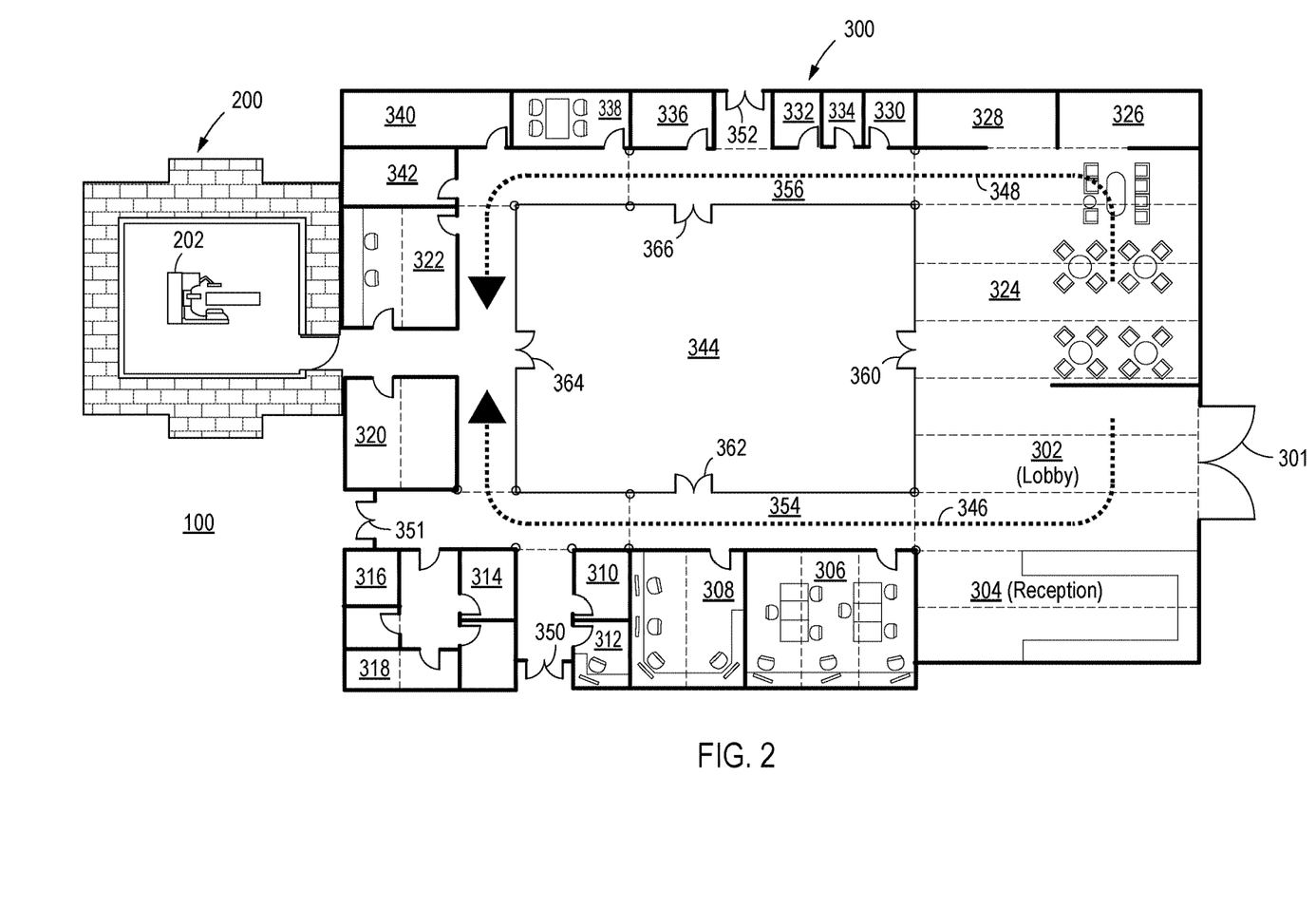
FIG. 2 is a top plan view of a radiotherapy center according to some embodiments of the disclosure.

Referring to FIGS. 1 and 2, an exemplary radiotherapy center 100 according to some embodiments of the disclosure will now be described. The radiotherapy center 100 includes a treatment room 200 and a plurality of functional rooms 300 adjacent to the treatment room 200. The treatment room 200 may contain a radiation machine 202 constructed or configured to produce high energy radiation for treatment of a patient in the room. By way of example, the radiation machine 202 located in the treatment room 200 can be a medical linear accelerator capable of generating radiation having energy ranging from 4 MV to 20 MV for treatment of tumors. The plurality of functional rooms 300 may include, by way of example, a lobby area 302, a reception area 304, an administration office 306, a treatment planning room 308, a meeting room 310, an office 312, a locker room 314, a cleaning room 316, staff restrooms 318, a storage room 320, and a treatment control room 322. The plurality of functional rooms 300 may further include a patient and family waiting area 324, a pantry room 326, a nurse station 328, restrooms 330, 332, a utility room 334, a consultation room 336, a sub-waiting room 338, an auxiliary or computer server room 340, and a change room 342. It should be noted that the design of the plurality of functional rooms 300 is flexible and the number of rooms is fully scalable based on the need of the radiotherapy center 100. The plurality of the functional rooms 300 may be arranged in a quadrangle configuration, surrounding a central atrium or courtyard 344. Alternatively, the plurality of functional rooms 300 may be arranged in a circular configuration or any other suitable configurations.

Referring to FIGS. 3-6, the treatment room 200, also often referred to as radiation vault or bunker, is designed or constructed to provide adequate attenuation to protect personnel outside the treatment room 200. The personnel might be staff, members of general public, or other patients. According to some embodiments of the disclosure, the treatment room 200 may be constructed with prefabricated, modular radiation shielding blocks. The modular radiation shielding blocks can be prefabricated in a factory and transported by land, air, or sea to the site for assembly. Because the design, engineering, and fabrication of the shielding blocks are carried out in a controlled factory environment, the radiation shielding performance can be guaranteed. The prefabricated, radiation shielding blocks also allow a fast, clean, and dry construction on site. It provides a cost effective solution when compared to conventional pour-in-place methodologies for constructing radiation bunkers on site. The prefabricated, modular radiation shielding blocks may be stackable and joined together in such a way that there is no direct straight line of passage through the joins. The prefabricated, modular radiation shielding blocks may be sized in certain units and assembled to form an entire side of the room, such as side walls 204, 206, 208, 210 and roof 212 as shown. In some embodiments, the stackable shielding blocks may be configured and pre-stacked into modules. The modules can then be craned into positions to form the entire shielding structure. The shielding structure constructed with the prefabricated modular shielding blocks can ensure that the radiation dose levels to the public and occupational personnel outside the shielding structure are below the limits as regulated by a state government or as recommended by a national or international organization. For example, the dose rate at the public area outside the shielding structure or vault can be controlled under 2.5 pSv/hr (instantaneous dose rate), which meets the regulations according to GBZ/T201.1-2007 in China. Alternatively, the radiation dose limits can be controlled below 0.02 mGy per week for uncontrolled areas or 0.1 mGy per week for controlled areas, which meets the regulations in the United States.

The materials can be selected and the thickness of the shielding blocks or stacked shielding blocks 204-212 can be calculated such that adequate attenuation of radiation can be provided. Computer software known in the art can be used for shielding calculation, taking into account of the energy specification of the radiation machine, the workload, the use factor, and occupancy factor, etc. In general, the design of the prefabricated, radiation shielding blocks or stacked shielding blocks 204-212 is such to provide radiation attenuation and maintain radiation dose levels outside the treatment room 200 below 0.02 mGy per week for uncontrolled areas or 0.1 mGy per week for controlled areas.

Suitable materials for constructing the radiation shielding blocks 204-212 include concrete, lead, steel, polyethylene, paraffin, earth, wood, rebar, foam ties, and any combination thereof. In some preferred embodiments, the radiation shielding blocks 204-212 of the disclosure are constructed with normal concrete ($\leq 2.35$ g/cm$^3$) or heavy concrete ($>2.35$ g/cm$^3$), or with a material comprising normal concrete or heavy concrete and other elements or additives listed above. In some preferred embodiments, the radiation shielding blocks are made of a material comprising cement and high density quartz.

The modular radiation shielding blocks 204-212 can be prefabricated using any suitable methods known in the art, including precasting. Precasting of concrete is well known in the art and thus its detailed description is omitted here in order to avoid unnecessary obscuring the description of embodiments of the disclosure.

Figure 3:
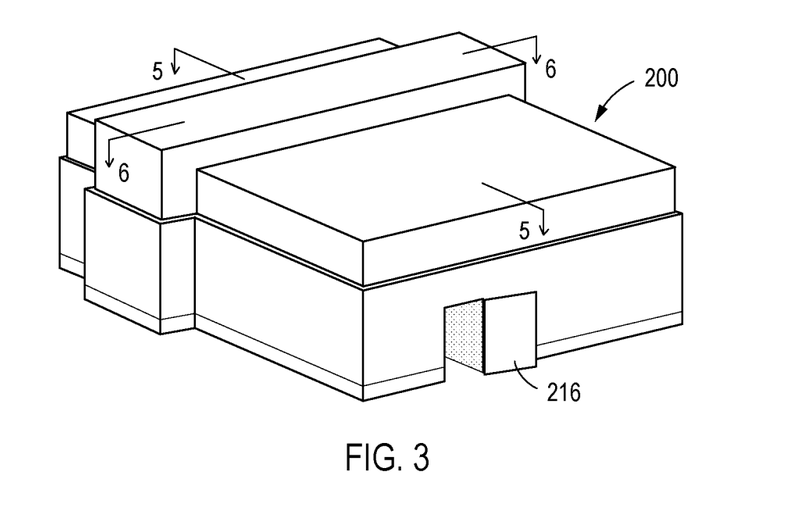
FIG. 3 is a perspective view of a treatment room according to some embodiments of the disclosure.
Figure 4:
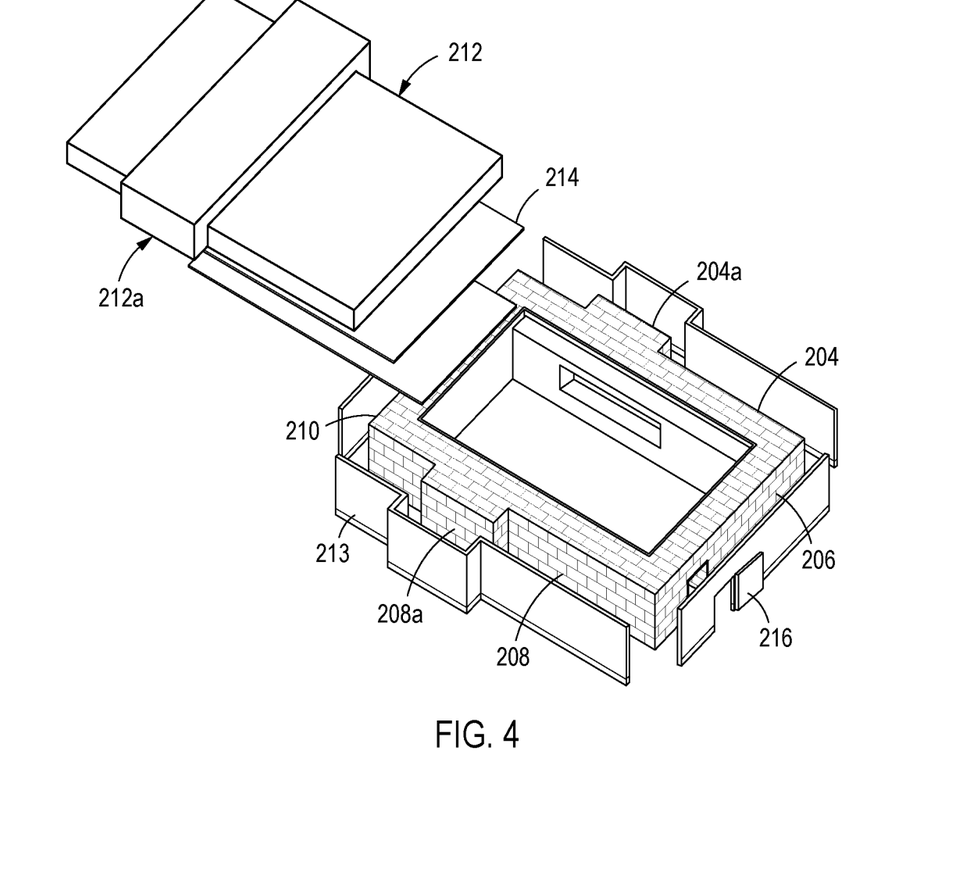
FIG. 4 is an exploded view of a treatment room according to some embodiments of the disclosure.
Figure 5:
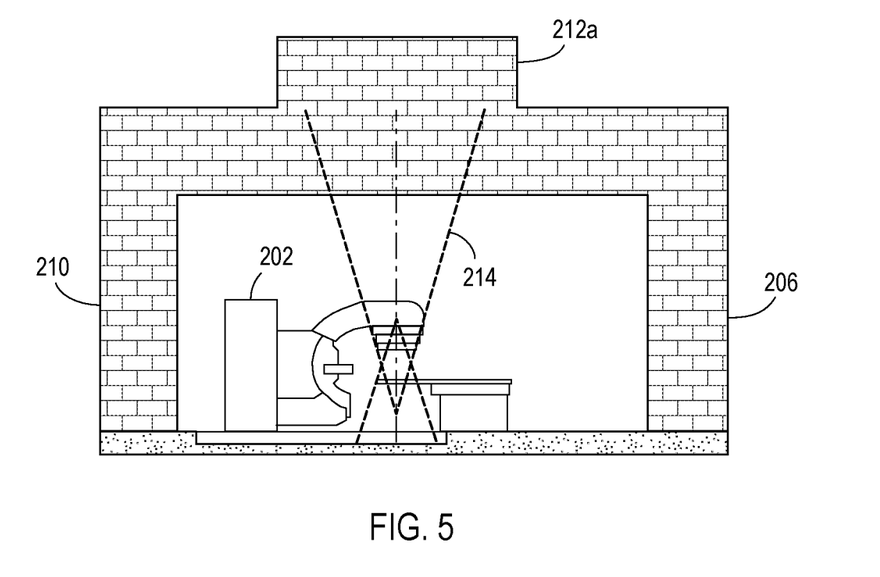
FIG. 5 is a cross-sectional view of a treatment room taken along line 5-5 in FIG. 3 according to some embodiments of the disclosure.
Figure 6:
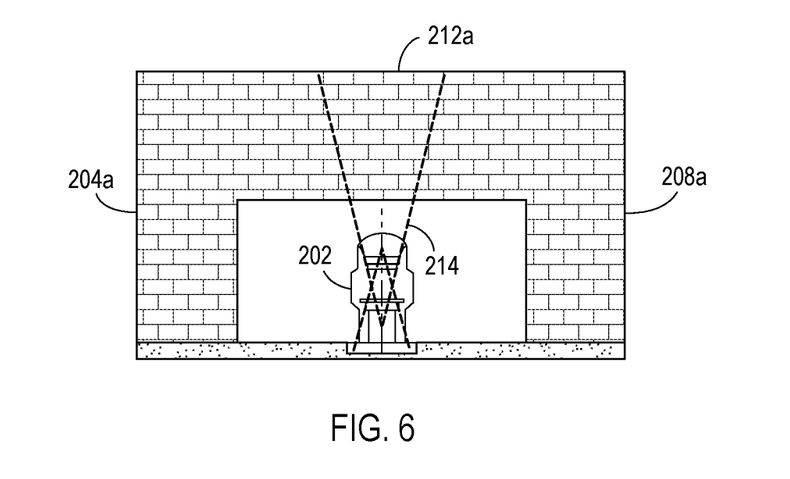
FIG. 6 is a cross-sectional view of a treatment room taken along line 6-6 in FIG. 3 according to some embodiments of the disclosure.

The prefabricated, modular radiation shielding blocks may be configured and pre-stacked into modules, e.g. in the form an entire side or roof of the treatment room 200. By way of example, the treatment room 200 may be designed generally in a rectangular shape, and each of the front, back, left, and right sides of the treatment room 200 and the roof of the treatment room 200 may be covered by a module of pre-stacked shielding blocks. The prefabricated modules of stackable shielding blocks may be transported to the site and craned into positions to form the entire shielding structure.

The treatment room 200 may further include pre-formed cladding panels 213 to protect the radiation shielding blocks 204-212 from weathering. Other components such as a ceiling system 214, flooring system, lighting and electrical system or the like may be provided in the treatment room 200.

The treatment room 200 or the stacked shielding blocks 204-212 may include relatively thicker sections 204*a*, 208*a*, 212*a* to form primary barriers intercepting the maximal radiation field of the radiation machine 202. The maximal radiation field 214 of the radiation machine 202 is indicated by the dashed lines in FIGS. 5 and 6 in the direction from the radiation source to the patient. In embodiments where the radiation machine 202 is capable of rotating around the patient in 360 degrees, primary barriers may be provided for all positions in the side walls and roof at which the radiation beam may be directed.

The treatment room 200 can be of direct entrance type with a shielding door 216 attached to the entrance of the room. Optionally, the treatment room 200 may include an entrance maze (not shown), forming an additional shielding for a person immediately outside the entrance.

Returning to FIGS. 1-2, the radiotherapy center 100 may include a plurality of functional rooms 300 adjacent to the treatment room 200. The plurality of functional rooms 300 may be arranged in a quadrangle configuration, surrounding a central atrium or courtyard 344 with some kind of landscape. Alternatively, the plurality of functional rooms 300 may be arranged in any other suitable configurations such as a circular configuration. The plurality of functional rooms 300 may be arranged to form a clinician flow 346 and a patient flow 348 as indicated by the directional arrows in FIG. 2. The patient flow 348 may be separated from the clinician flow 346. A separate flow for patients or clinicians may help avoid the crowd and increase flow efficiency in the facility.

By way of example, for the patient flow 348, the patient may go through the following route:

Main entrance 301→lobby 302→reception 304→waiting area 324→restroom 330/332 (if needed)→consultation/exam room 336→sub-waiting room 338→changing room 342→treatment room 200

For the clinician flow 346, the clinical staff may go through the following route:

Main entrance 301→lobby 302→office 306→treatment planning room 308→meeting room 310→storage room 320→control room 322

Additional entrances/exits 350, 352 may be provided in the clinician flow 346 and/or patient flow 348. For example, the patient may leave at an exit 352 if the patient considers privacy is needed. Clinical staff can also utilize the entrance/exit 352 as another option to avoid passing through the crowd at the main entrance area. These optional exits 350, 352 can also serve as fire escape routes.

Figure 7:
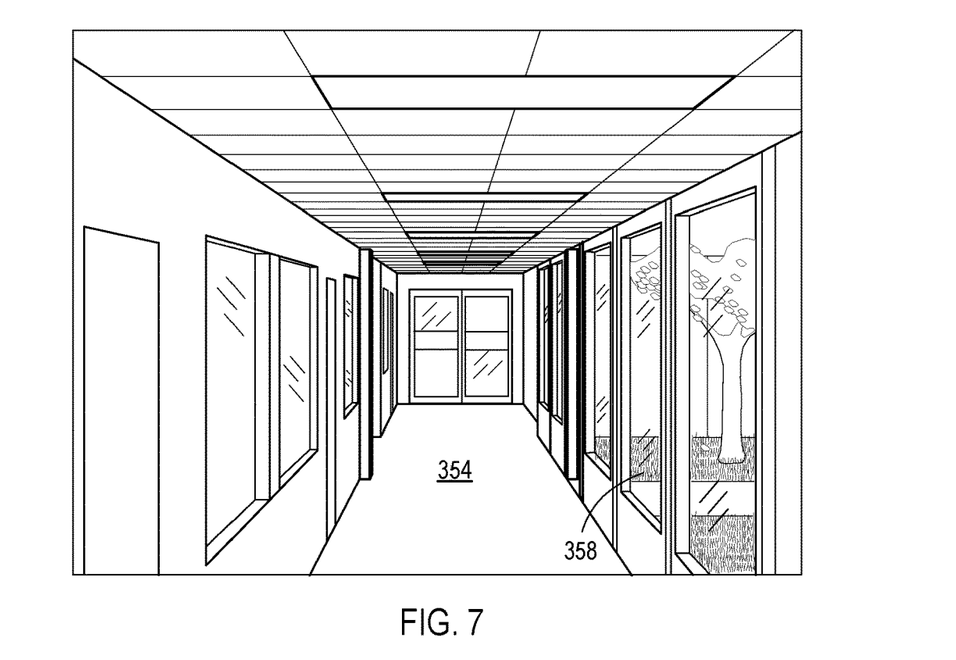
FIG. 7 schematically shows a clinician corridor between clinician rooms and a central atrium according to some embodiments of the disclosure.
Figure 8:
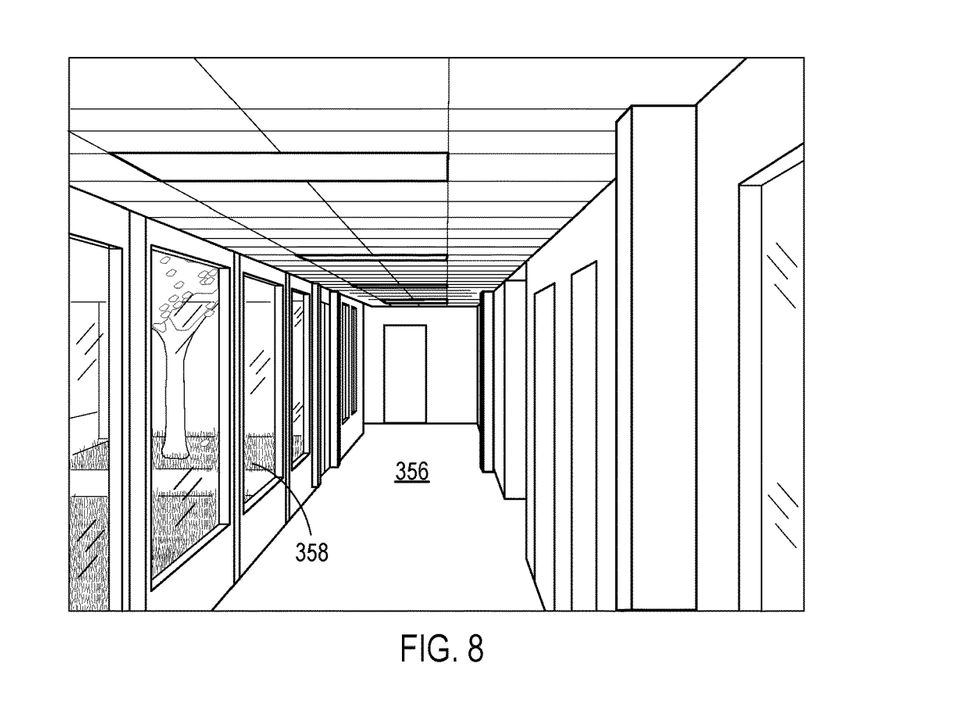
FIG. 8 schematically shows a patient corridor between patient rooms and a central atrium according to some embodiments of the disclosure.

The radiotherapy center 100 may include one or more corridors 354, 356 between the courtyard 344 and the plurality of functional rooms 300 surrounding the courtyard 344. FIG. 7 shows a clinician corridor 354, or a corridor for the clinician flow. FIG. 8 shows a patient corridor 356, or a corridor for the patient flow. The clinician and/or patient corridors 354, 356 may include one or more windows or a glass structure 358 to allow natural light to transmit into the corridors 354, 356. The clinician and/or patient corridors 354, 356 may also include one or more doors 360, 362, 364, 366 (FIG. 2) to allow access to the central atrium 344. The glass structure 358 surrounding the central atrium 344 helps capture natural sunlight into the facility so that people working inside the facility have a feel of spacious environment although the space inside their cubes may be limited. Natural light may help comfort the patient's mind and make them feel easy when anxiety is common for some people who receive treatment. It also helps eliminate stress from the staff. The central atrium 344 may be an open space where a view of some landscape can be provided to people inside the facility.

Figure 9:
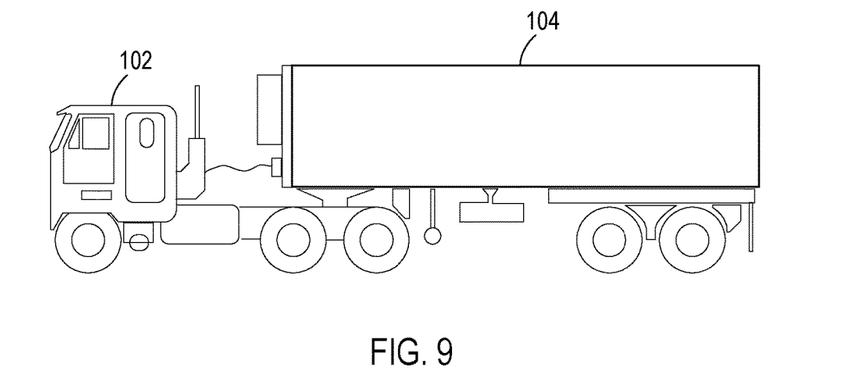
FIG. 9 schematically shows a truck that can be used to transport prefabricated, modular radiation shielding blocks and/or functional modules according to some embodiments of the disclosure.

The plurality of functional rooms 300 may be constructed or assembled from a plurality of prefabricated modules. The prefabricated modules can be constructed in a factory and transported to the site by land, air, or sea for assembly. FIG. 9 schematically shows a truck 102 capable of carrying a freight container 104, which can be used to transport the prefabricated modules. Each of the prefabricated modules may have an outer dimension approximately same as a size of the freight container 104. By way of example, the prefabricated modules can be sized such that they can be transported by a 20-foot container having dimensions of 5,900 mm long, 2,350 mm wide and 2,690 mm high. In another exemplary embodiment, the prefabricated modules can be sized such that they can be transported by a 40-foot container having dimensions of 12,040 mm long, 2,350 mm wide and 2,690 mm high.

Figure 10:
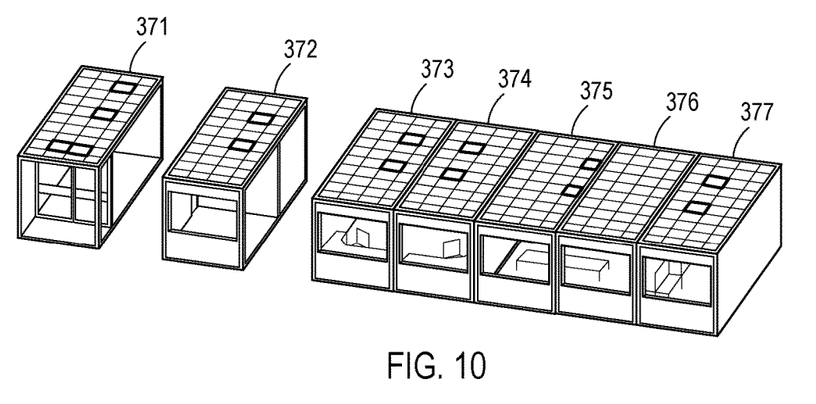
FIG. 10 schematically shows a plurality of prefabricated functional modules that can be transported by a freight container according to some embodiments of the disclosure.
Figure 11:
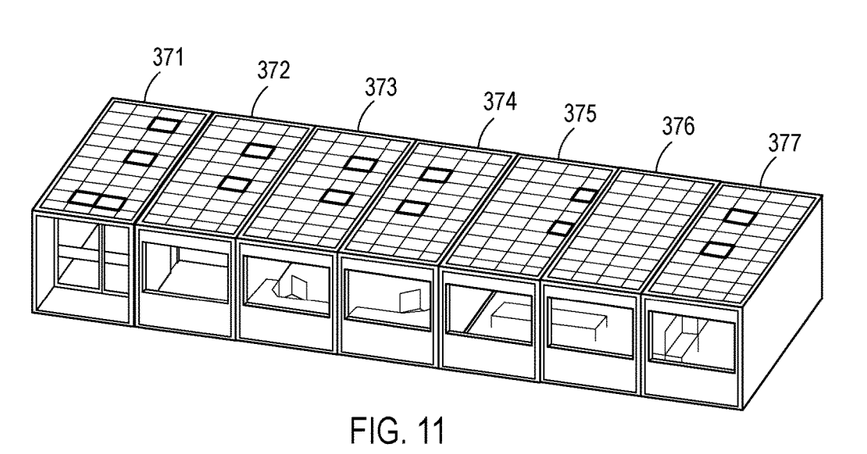
FIG. 11 schematically shows the assembly and integration of the functional modules shown in FIG. 10 according to some embodiments of the disclosure.

The prefabricated modules can be designed and fabricated such that one prefabricated module forms one functional room. FIG. 10 schematically shows seven prefabricated modules 371-377 that can be transported by a 40-foot container. FIG. 11 schematically shows the assembly and integration of the seven functional modules 371-377 on site, forming seven functional rooms.

Figure 12:
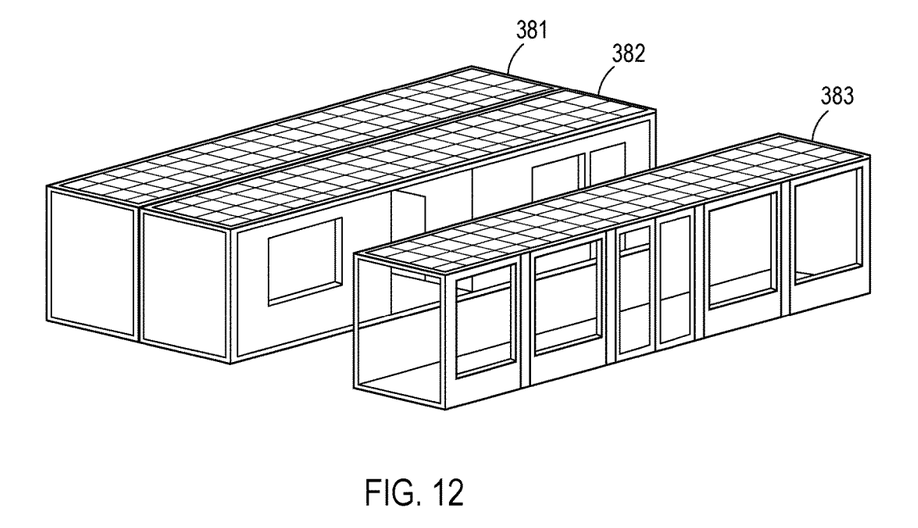
FIG. 12 schematically shows a plurality of prefabricated functional modules that can be transported by a freight container according to some other embodiments of the disclosure.
Figure 13:
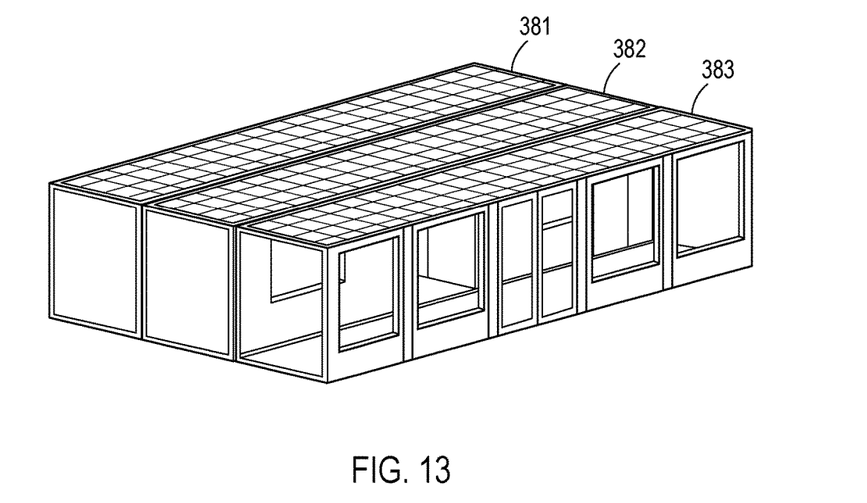
FIG. 13 schematically shows the assembly and integration of the functional modules shown in FIG. 12 according to some other embodiments of the disclosure.

In some embodiments, two or more prefabricated modules may be assembled or connected to form one functional room, or alternatively one prefabricated module may be further divided to form two or more functional rooms. FIG. 12 schematically shows three prefabricated modules 381-383 that can be transported by a 40-foot container. FIG. 13 schematically shows the assembly and integration of the three functional modules, forming e.g. a section of a corridor 383 and one or more functional rooms 381-382.

The prefabricated modules may include a frame structure, with wall panels and optionally windows and/or doors being installed ready for assembly and integration on site using associated components provided. Alternatively, the prefabricated modules may be provided such that one or more components such as windows and/or doors may be installed on site after the assembly and integration of the prefabricated modules.

For assembly of the treatment room 200 and the plurality of functional rooms 300, a suitable foundation such as a concrete slab may be first created on site. A prefabricated banker steel structure (not shown) may be anchored to the foundation. The banker steel structure may be configured to support and stabilize the plurality of prefabricated, modular radiation shielding blocks. The steel structure may also be configured to accommodate a base frame (not shown) for a radiation machine installation. The radiation machine may be installed in the base frame on site. Alternatively, the radiation machine may be preinstalled with the base frame and banker steel structure in a factory and then transported to the site. After the concrete foundation is properly leveled, the prefabricated, modular radiation shielding blocks, e.g. in the form of prefabricated modules, may be craned into position and connected to form the treatment room. Alternatively, the stackable shielding blocks can be stacked up one by one to form the entire shielding structure including the roof and walls. A plurality of functional rooms may also be formed on the foundation by craning the prefabricated modules into position and connecting the modules using suitable components. The whole structure may be covered with pre-formed cladding panels, metal roofing, glass wall and/or skylight to protect the structure from weathering while allows for natural light.

Figure 14:
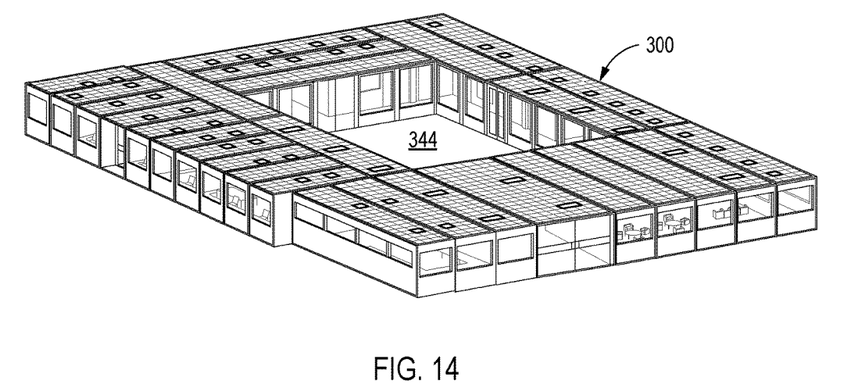
FIG. 14 schematically shows a plurality of functional rooms in a radiotherapy center formed by assembling and integrating a plurality of prefabricated modules on site according to some embodiments of the disclosure.

FIG. 14 schematically shows a plurality of functional rooms 300 formed by assembling and integrating a plurality of prefabricated modules on site. In this exemplary embodiment, the functional rooms 300 are arranged in a quadrangle configuration surrounding a central atrium 344.

Figure 15:
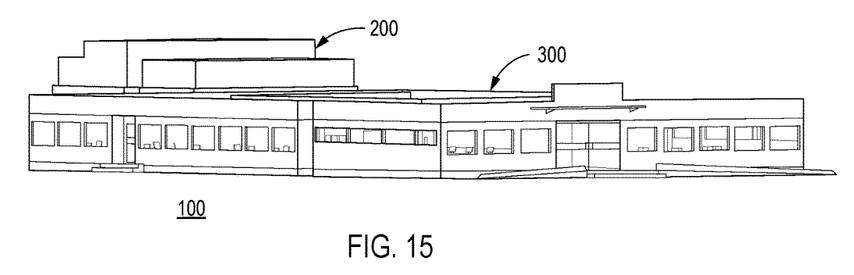
FIG. 15 is a perspective view of a radiotherapy center comprising a treatment room and a plurality of functional rooms constructed according to an exemplary method of the disclosure.

FIG. 15 schematically shows a radiotherapy center 100 constructed according to embodiments of the disclosure, including a treatment room 100 formed with prefabricated, modular radiation shielding blocks, and a plurality of functional rooms 300 formed with prefabricated modules.

Those skilled in the art will appreciate that various modifications may be made within the spirit and scope of the invention. For example, the radiotherapy center 100 may also include rooms and equipment for diagnostics. The radiotherapy center 100 may provide Wi-Fi connection and/or computers with internet connection in reception area and waiting rooms. The radiotherapy center 100 may also include vending machines and/or cafeteria. All these or other variations and modifications are contemplated by the inventors and within the scope of the invention.

What is claimed is:

1. A radiotherapy center, comprising:
a treatment room; and
a radiation machine located in the treatment room,
wherein the treatment room is constructed with materials comprising a plurality of prefabricated, modular radiation shielding blocks, wherein the plurality of prefabricated, modular radiation shielding blocks are pre-stacked in the form of one or more modules, each of said one or more modules transported as a unit of the treatment room to a site for constructing the treatment room.

2. The radiotherapy center of claim 1, wherein the module is sized to form an entire side of the treatment room having a rectangular shape.

3. The radiotherapy center of claim 1, wherein the prefabricated, modular radiation shielding blocks are made of a material comprising concrete.

4. The radiotherapy center of claim 1, wherein the prefabricated, modular radiation shielding blocks are made of a material comprising cement and high density quartz.

5. The radiotherapy center of claim 1, wherein the treatment room is constructed with the materials further comprising a steel structure supporting the plurality of prefabricated, modular radiation shielding blocks.

6. The radiotherapy center of claim 1, further comprising a plurality of functional rooms adjacent to the treatment room, wherein the plurality of functional rooms are constructed from a plurality of prefabricated modules.

7. The radiotherapy center of claim 6, wherein the plurality of functional rooms comprise a lobby area, a reception area, a waiting area, a restroom, a change room, an office, a consultation room, a treatment planning room, a treatment control room, and a computer server room.

8. The radiotherapy center of claim 6, further comprising a central atrium open to the natural environment, and the plurality of functional rooms are arranged to surround the central atrium.

9. The radiotherapy center of claim 8, wherein the plurality of functional rooms are arranged in a quadrangle configuration.

10. The radiotherapy center of claim 8, wherein the plurality of functional rooms are arranged such to provide a patient flow and a clinician flow that are separated from each other.

11. The radiotherapy center of claim 8, further comprising one or more corridors between the plurality of functional rooms and the central atrium.

12. The radiotherapy center of claim 11, wherein the one or more corridors comprise a glass structure on a side adjacent to the central atrium to allow natural light to transmit into the one or more corridors, and/or one or more doors to allow access to the central atrium.

13. The radiotherapy center of claim 1, wherein the center is movable to another location.

14. A structure, comprising:
a room to be occupied by a radiation machine and a subject to be treated by the radiation machine; and
a plurality of prefabricated, modular radiation shielding blocks enclosing the room, wherein the plurality of prefabricated, modular radiation shielding blocks are configured to adequately attenuate radiation produced by the radiation machine,
wherein at least some of the plurality of prefabricated, modular radiation shielding blocks are pre-stacked in the form of a module transported as a unit of the room to a site for constructing the structure.

15. The structure of claim 14, wherein each of the modules is sized to form an entire side of the room having a cuboid shape.

16. The structure of claim 14, wherein the prefabricated, modular radiation shielding blocks are made of a material comprising concrete.

17. A radiation shielding module, wherein
the radiation shielding module comprises a plurality of prefabricated modular radiation shielding blocks stacked one on another, and is transported as a unit of a treatment room to a site for constructing the treatment room for radiotherapy, and
the radiation shielding module is configured to adequately attenuate radiation produced by a radiation machine to be occupied in the treatment room.

18. The radiation shielding module of claim 17, wherein the radiation shielding module is in the form of a side wall or roof.

19. The radiation shielding module of claim 18, wherein the radiation shielding module is sized to form an entire side of the treatment room having a cuboid shape.

20. The radiation shielding module of claim 17, wherein the radiation shielding module is fabricated by a plurality of radiation shielding blocks made of a material comprising concrete.

21. The radiation shielding module of claim 20, wherein the plurality of radiation shielding blocks are made of a material comprising a combination of concrete and quartz.

22. A method of constructing a radiotherapy center, the method comprising:
   providing a plurality of prefabricated radiation shielding modules to a site selected for a radiotherapy center, wherein each of the radiation shielding modules comprises a plurality of prefabricated, modular radiation shielding blocks stacked one on another; and
   constructing a treatment room using the plurality of prefabricated, radiation shielding modules; and
   providing a radiation machine in the treatment room, wherein each of the radiation shielding modules is transported as a unit of the treatment room to the site.

23. The method of claim 22, wherein the plurality of prefabricated radiation shielding modules are constructed with a plurality of radiation shielding blocks in a factory and transported to the site using a 20-foot container or a 30 feet container.

24. The method of claim 22, further comprising providing a plurality of prefabricated functional modules to the site, and constructing a plurality of functional rooms adjacent to the treatment room using at least some of the plurality of prefabricated functional modules.

25. The method of claim 22, wherein the plurality of prefabricated modules are fabricated in a factory and transported to the site using a 20-foot container or a 30 feet container.

* * * * *

UNITED STATES PATENT AND TRADEMARK OFFICE
CERTIFICATE OF CORRECTION

PATENT NO. : 10,265,232 B2
APPLICATION NO. : 15/553158
DATED : April 23, 2019
INVENTOR(S) : Chung Chee Yim et al.

Page 1 of 1

It is certified that error appears in the above-identified patent and that said Letters Patent is hereby corrected as shown below:

In the Specification

At Column 6 Line 33, please replace "pSv/hr" with -µSv/hr-.

Signed and Sealed this
Twenty-fourth Day of September, 2019

Andrei Iancu
*Director of the United States Patent and Trademark Office*